(12) United States Patent
Yang et al.

(10) Patent No.: US 8,044,250 B2
(45) Date of Patent: *Oct. 25, 2011

(54) MANUFACTURE OF 1,1,1,2,3,3-HEXAFLUOROPROPANE AND 1,1,1,2-TETRAFLUOROPROPANE VIA CATALYTIC HYDROGENATION

(75) Inventors: Shuwu Yang, Richmond, CA (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 408 days.

This patent is subject to a terminal disclaimer.

(21) Appl. No.: 12/264,735

(22) Filed: Nov. 4, 2008

(65) Prior Publication Data

US 2009/0131727 A1      May 21, 2009

Related U.S. Application Data

(60) Provisional application No. 61/003,449, filed on Nov. 16, 2007.

(51) Int. Cl.
*C07C 19/08*      (2006.01)
(52) U.S. Cl. ..................................................... 570/134
(58) Field of Classification Search ........................ None
See application file for complete search history.

(56) References Cited

U.S. PATENT DOCUMENTS

| 5,679,875 | A | 10/1997 | Aoyama et al. ............... 570/156 |
| 5,714,654 | A * | 2/1998 | Yamamoto et al. ........... 570/170 |
| 6,506,950 | B1 | 1/2003 | Krespan |
| 2007/0179324 | A1 | 8/2007 | Van Der Puy et al. |

FOREIGN PATENT DOCUMENTS

| JP | 05148171 | 6/1993 |
| JP | 8165256 | 6/1996 |
| JP | 8169851 | 7/1996 |
| WO | WO9427940 | 12/1994 |
| WO | WO2007086972 | 8/2007 |

OTHER PUBLICATIONS

Knunyants et al., "Communication 13. Catalytic Hydrogenation of Perfluoro Olefins" Bull. Acad. Sci. USSR Div. Chem Sci. 1960, pp. 1312-1317, ISSN 1066-5285.*
Database CAPLUS Chemical Abstracts Service, Columbus, Ohio, US; Database Accession No. 2008:398508, Abstract of Xu et al., CN 101148395: "Method for preparation of 1,1,1,2,3,3-hexafluoropropane from 1,1,1,2,3,3-hexafluoropropylene and hydrogen gas".*
Knunyants I.L. et al., 'Communication 13. Catalytic Hydrogenation of Perfluoro Olefins', Bull. Acad. Sci. USSR Div. Chem Sci. 1960, pp. 1312-1317, ISSN 1066-5285.

* cited by examiner

*Primary Examiner* — Karl J Puttlitz
(74) *Attorney, Agent, or Firm* — Bruce Bradford

(57) ABSTRACT

A process for producing hydrofluorocarbon compounds represented by the following formula:

$$CF_3CHFCH_{m+1}F_n$$

wherein m is 0 or 2; n is 0 or 2; and m+n=2. The process has the step of contacting, i.e., reacting, hydrogen with a precursor compound represented by the following formula:

$$CF_3CF=CH_mF_n$$

wherein m is 0 or 2; n is 0 or 2; and m+n=2. The contact is carried out in the presence of a solid catalyst and in the presence or absence of an inert gas. The catalyst is selected from the group consisting of: Fe, Co, Ni, Cu, Cr, Ru, Rh, Ag, Re, Os, Ir, Pt, Au, Sn, and any combinations thereof. For the hydrogenation of 1234yf to 254eb, Pd can also be used as catalyst in addition to the other above-referenced metals. These metals are preferably supported on a carrier such as activated carbon.

28 Claims, No Drawings

MANUFACTURE OF 1,1,1,2,3,3-HEXAFLUOROPROPANE AND 1,1,1,2-TETRAFLUOROPROPANE VIA CATALYTIC HYDROGENATION

CROSS-REFERENCED APPLICATION

This application claims priority to U.S. Provisional Patent Application, Ser. No. 61/003,449, filed on Nov. 16, 2007, which is incorporated herein by reference in its entirety.

BACKGROUND

1. Field of the Disclosure

The present disclosure relates to the manufacture of 1,1,1,2,3,3-hexafluoropropane and 1,1,1,2-tetrafluoropropane via catalytic hydrogenation.

2. Description of the Related Art 1,1,1,2,3,3-hexafluoropropane (236ea) and 1,1,1,2-tetrafluoropropane (254eb) are useful as alternatives to CFCs and HCFCs, which have been used as refrigerants, blowing agents and solvents.

236ea and 254eb can be synthesized respectively by hydrogenation of hexafluoropropene (HFP) and 1,1,1,2-tetrafluoropropene (1234yf), respectively. For the hydrogenation of HFP to 236ea, catalysts of $Pd/Al_2O_3$ (Invest. Akand. Nauk s.s.s.r., Otdel. Kim. Nauk. 1960, 1 412-18.), Pd/C (Japanese Published Applications JP8165256 and JP8169851) and $Pd/BaSO_4$ (Japanese Published Application JP8165256) have been reported. Use of promoted palladium catalysts in the absence of HF have been reported in U.S. Pat. No. 5,679,875.

It would be desirable to develop other hydrogenation catalysts that offer good performance, long life and low cost.

SUMMARY

According to the present disclosure, there is provided a process for producing hydrofluorocarbon compounds represented by the following formula:

$$CF_3CHFCH_{m+1}F_n$$

wherein m is 0 or 2; n is 0 or 2; and m+n=2. The process has the step of contacting, i.e., reacting, hydrogen with a precursor compound represented by the following formula:

$$CF_3CF=CH_mF_n$$

wherein m is 0 or 2; n is 0 or 2; and m+n=2. The contact is carried out in the presence of a solid catalyst and in the presence or absence of an inert gas. The catalyst is selected from the group consisting of Fe, Co, Ni, Cu, Cr, Ru, Rh, Ag, Re, Os, Ir, Pt, Au, Sn, and any combinations thereof. For the hydrogenation of 1234yf to 254eb, Pd can also be used as catalyst in addition to the other above-referenced metals. These metals are preferably supported on a carrier such as activated carbon.

DETAILED DESCRIPTION OF THE PREFERRED EMBODIMENT

The process of the present disclosure employs catalytic hydrogenation to produce hydrofluorocarbon compounds represented by the following formula:

$$CF_3CHFCH_{m+1}F_n$$

wherein m is 0 or 2; n is 0 or 2; and m+n=2.

The process has the step of contacting, i.e., reacting, hydrogen with a precursor compound represented by the following formula:

$$CF_3CF=CH_mF_n$$

wherein m is 0 or 2; n is 0 or 2; and m+n=2. The contact is carried out in the presence of a metal catalyst and in the presence or absence of an inert gas.

The process can include the following reactions:

(1) $CF_3CF=CF_2 (HFP) + H_2 \rightarrow CF_3CHF-CHF_2 (236ea)$ (wherein m=0, n=2) and $CF_3CF=CH_2 (1234yf) + H_2 \rightarrow CF_3CHF-CH_3 (254eb)$ (wherein m=2, n=0).

The following catalysts can be used in the hydrogenation reactions: Fe, Co, Ni, Cu, Cr, Ru, Rh, Ag, Re, Os, Ir, Pt, Au, Sn, and any combinations thereof. For the hydrogenation of 1234yf to 254ed, Pd can also be used as catalyst in addition to the other above-referenced metals.

If desired, a catalyst promoter/modifier can be used to modified catalyst reactivity and stability. When used together with other metals in a catalyst, Cr or Sn can behave as a promoter/modifier.

The catalyst may be supported or unsupported. Examples of unsupported catalysts include Raney Ni and Cu—Cr. Examples of catalyst supports include C (carbon) and carbonaceous materials, $Al_2O_3$, $SiO_2$, MgO, $ZrO_2$, $TiO_2$, ZnO, $CeO_2$, $La_2O_3$, metal fluorides, (e.g., $MgF_2$, $AlF_3$, $LaF_3$), and $BaSO_4$. A preferred carbonaceous material is activated carbon. Preferred supports are activated carbon and $Al_2O_3$. For a supported catalyst, on a support ranges from about 0.01 to about 50 wt. %, preferably about 0.1 to about 25 wt. %, and most preferably about 1 to about 10 wt. % based on the total weight of the metal on the support.

The catalysts, whether supported or unsupported, are preferably calcined in an inert gas, such as nitrogen, helium, and/or argon, at a temperature of about 100° C. to about 750° C., preferably at about 200° C. to about 600° C., and more preferably at about 350° C. to about 500° C. For most catalysts, after calcination and before reaction, the catalysts are treated/activated with hydrogen or an inert gas, such as nitrogen, helium, and/or argon, or a combination thereof. The treatment is carried out at a temperature of 0° C. to about 600° C., preferably at about 20° C. to about 500° C., and more preferably at about 200° C. to about 400° C.

The hydrogenation reactions may be carried out in vapor phase or liquid phase. The $CF_3CF=CH_mF_n$ compound can be in gas or liquid state depending on the conditions (i.e., temperature and pressure).

The process may be carried out in a reactor in a continuous or batch manner. The reactor can be a continuous fixed-bed reactor (conventional or trickle-bed), a moving-bed reactor, a batch reactor or a CSTR (continuous stirred tank reactor). To gain a better control of reaction temperature, the feed can optionally be diluted with an inert gas (e.g., $N_2$, Ar, He) or by recycle of at least a part or portion of the product stream. The recycled product stream may contain products, such as 236ea or 254eb, or unreacted reactants ($CF_3CF=CH_mF_n$ and/or hydrogen). The feed can also be diluted with the target product in order to effectively control the heat generated during the exothermic hydrogenation reaction. In case a diluent of the feed is used, the volume ratio of the feed to the diluent is from 0.01 to 100, preferably from 0.05 to 20, and more preferably from 0.25 to 4. Alternately, the catalyst can be optionally diluted by bare support or metal packings when fixed-bed reactor is used.

The precursor compounds (hydrofluoropropenes and fluoropropenes), i.e., the $CF_3CF=CH_mF_n$ compounds, include $CF_3CF=CF_2$ (HFP) and $CF_3CF=CH_2$ (1234yf). The product hydrofluoropropanes include $CF_3CHF-CHF_2$ (236ea) and $CF_3CHF-CH_3$ (254eb).

The reaction is carried out at a temperature and pressure and for a contact time sufficient to effect conversion. Reaction temperature can range from about −30° C. to about 600° C., preferably at about 20° C. to about 400° C., and more preferably at about 60° C. to about 200° C. Reaction pressure can range from about 0.01 to about 200 atm and preferably at about 0.1 to about 50 atm. The hydrogen to $CF_3CF=CH_mF_n$ (HFP or 1234yf) molar feed ratio can range from about 0.1 to about 20, preferably from about 0.5 to about 10, and more preferably from about 1 to about 5. The contact time of the $CF_3CF=CH_mF_n$ compound with the catalyst can range from about 0.0001 second to about 100 hours and preferably from about 0.1 second to about 30 hours. In a continuous gas-solid phase reactor, the contact time is more preferably from about 1 second to about 10 minutes. In a batch liquid-solid reactor, the contact time is more preferably from about 5 hours to about 30 hours.

Conversion of the $CF_3CF=CH_mF_n$ compound is preferably from about 20% to about 100% and most preferably from about 70% to about 100%. Selectivity for the target hydrofluorocarbon, i.e., 236ea or 254eb, is preferably from about 20% to 100% and most preferably from about 70% to 100%.

The following are examples of the present disclosure and are not to be construed as limiting.

EXAMPLES

Preparation of Carbon Supported Metal (Metal/C) Catalysts

Designated amount of metal salt was dissolved in deionized water (the amount of water was calculated from the pore volume of a support). After the salts were dissolved completely, designated amount of activated carbon (pre-dried at 100° C. to 120° C. for 12 hours (hr)) was slowly poured into the solution, or vice versa. The paste was stirred continuously to achieve homogeneous impregnation and then was put in a ventilation hood overnight to allow adequate impregnation. Subsequently, the impregnated sample was dried in an oven at 100° C. to 120° C. for 12 hours and calcined at 400° C. to 500° C. for 4 hours under a stream of nitrogen. The metal salts used for preparing Ni/C (nickel/activated carbon), Pd/C (palladium/activated carbon), Pt/C (platinum/activated carbon), Ru/C (ruthenium/activated carbon), Co/C (cobalt/activated carbon) and Cu/C (copper/activated carbon) were $Ni(NO_3)_2$, $Pd(NO_3)_2$, $H_2PtCl_6$, $RuCl_3$, $Co(NO_3)_2$ and $Cu(NO_3)_2$, respectively.

The activated carbon support used was pelletized Shirasagi C2X 4/6-2 from Japan EnviroChemicals, Ltd., which is a highly purified activated carbon support with a surface area above 1000 $m^2/g$ (square meters per gram) and an average pore diameter of 23 Å (angstroms).

About 25 ml of calcined catalyst were loaded in a ¾ inch monel tube reactor. The temperature of the reactor was measured by a 5-point thermocouple bundle (4 inch spacing between thermocouples) accommodated in a thermowell in the center of the reactor. Before reaction, the catalyst was first reduced with hydrogen at the conditions given in the examples below. After reduction, the reactor was cooled down to designated temperature and then organic reactants and hydrogen were introduced. Unreacted reactants and products were analyzed by on-line gas chromatography.

Example 1

Reactivity of Different Metal Catalysts

All catalysts tested were supported catalysts. Pt/C and Ru/C catalysts were diluted with monel packings and reduced at 200° C. for 2 hours before use. Ni/C, Co/C and Cu/C catalysts were reduced at 400° C. for 2 hours before introducing HFP (hexafluoropropene) feed. After reaction for 8 hours, the 0.5% Pt/C catalyst (0.5 weight percent platinum based on the total weight of the supported catalyst) gave 44.5% HFP conversion and 76.0% 236ea selectivity while 1% Ru/C exhibited 15.1% HFP conversion and 44.5% 236ea selectivity. For 10% Ni/C, the HFP conversion and 236ea selectivity were 32.4% and 92.7%, respectively. 10% Co/C was not as active as 10% Ni/C. 10% Co/C showed 4.8% HFP conversion and 43.1% 236ea selectivity at 200° C. 10% Cu/C was not active below 200° C. At 300° C., 10% Co/C showed 8.1% conversion and 94.9% selectivity, but the catalyst deactivated rapidly at this temperature, possibly due to the sintering of the copper particles. Table 1 sets forth the reactivity of some catalysts for the hydrogenation of HFP to 236ea.

TABLE 1

(Activity and selectivity of HFP to 236ea on different metal catalysts.)

| Catalyst | Catalyst amount | Temperature (° C.) | HFP conversion (%) | 236ea selectivity (%) |
|---|---|---|---|---|
| 0.5% Pt/C | 2 g + 10 g Monel packing | 100 | 44.5 | 76.0 |
| 1% Ru/C | 2 g + 10 g Monel packing | 100 | 15.1 | 44.5 |
| 10% Ni/C | 25 ml | 100 | 34.4 | 92.7 |
| 10% Co/C | 25 ml | 100 | 1.3 | 93.1 |
|  |  | 150 | 2.6 | 73.2 |
|  |  | 200 | 4.8 | 43.1 |
| 10% Cu/C | 25 ml | 200 | 0.2 | 97.2 |
|  |  | 250 | 2.9 | 96.7 |
|  |  | 300 | 8.1 | 94.9 |

*Reaction conditions: HFP feed rate: 20 g/h (grams/hour); $H_2$/HFP molar ratio = 1.2

Example 2

Effect of Nickel Loading on the Reactivity of Ni/C Catalyst

The reactivity of Ni/C catalysts at various Ni loadings was tested. Catalyst activity increased with increasing Ni loading from 2 wt. % (weight percent) to 5 wt. % but decreased as Ni loading increased to 10 wt. %. Catalyst selectivity to 236ea did not change much with Ni loading, all at about 95%. 5% Ni/C gave 57.0% HFP conversion, which was more active than 2% Ni/C and 10% Ni/C. The results are set forth in Table 2.

TABLE 2

(Effect of Ni loading on activity, selectivity and productivity of Ni/C catalysts)

| Catalyst | HFP conversion (%) | 236ea selectivity (%) |
|---|---|---|
| 2% Ni/C | 38.1 | 95.1 |
| 5% Ni/C | 57.0 | 94.1 |
| 10% Ni/C | 30.4 | 96.5 |

*Reaction conditions: 25 ml catalyst; 100° C.; HFP feed rate: 20 g/h; $H_2$/HFP molar ratio = 2; catalyst reduced at 400° C. Reacted for 8 hrs.

Example 3

Effect of Reduction Temperature on the Reactivity of Ni/C Catalyst

Table 3 shows the reactivity of 5% Ni/C catalyst reduced at various temperatures. In the beginning of the reaction (0 to 5 hours), catalyst pre-reduced at higher temperature showed higher activity. However, the effect of reduction temperature on catalyst activity was not significant after the catalyst was run for more than 5 hrs. The catalyst reduced at 200° C. did show lower selectivity to 236ea than the catalyst reduced at 300° C. and 400° C.

TABLE 3

(Effect of catalyst reduction temperature on activity, selectivity and productivity of 5% Ni/C catalyst)

| Reduction temperature (° C.) | HFP conversion (%) | 236ea selectivity (%) | 236ea productivity (lb/h/ft$^3$) |
|---|---|---|---|
| 200 | 58.1 | 74.1 | 21.8 |
| 300 | 57.8 | 94.3 | 27.6 |
| 400 | 57.0 | 94.1 | 27.2 |

*Reaction conditions: 25 ml catalyst; 100° C.; HFP feed rate: 20 g/h; H$_2$/HFP molar ratio = 2. Reacted for 10 hrs.

Example 4

Effect of HFP Feed Rate on the Reactivity of Ni/C Catalyst

The effect of HFP feed rate on the reactivity of 5% Ni/C was investigated. The higher the HFP feed rate, the shorter the contact time. When the HFP feed rate increased from 5 g/h to 10 g/h and 20 g/h, the activity of 5% Ni/C decreased monotonically from 96.7% to 83.4% and 57.0%, respectively. No significant change in selectivity was observed with increasing HFP feed rate. A similar trend was observed for 10% Ni/C catalyst. Low HFP feed rate (long contact time) favored the hydrogenation reaction. Results are set forth in Table 4

TABLE 4

(Effect of HFP feed rate on the activity, selectivity and productivity of 5% Ni/C catalyst)

| HFP feed rate (g/h) | HFP conversion (%) | 236ea selectivity (%) | 236ea productivity (lb/h/ft$^3$) |
|---|---|---|---|
| 5 | 96.7 | 97.8 | 12.0 |
| 10 | 83.4 | 96.0 | 20.3 |
| 20 | 57.0 | 94.1 | 27.1 |

*Reaction conditions: 25 ml catalyst; 100° C.; H$_2$/HFP molar ratio = 2; catalyst reduced at 400° C. Reacted for 10 hrs.

Example 5

Effect of H$_2$ to HFP Atomic Ratio on the Reactivity of Ni/C Catalyst

The effect of H$_2$ to HFP molar ratio on the reactivity of 5% Ni/C catalyst was investigated. With increasing H$_2$/HFP molar ratio, catalyst activity increased linearly. Catalyst selectivity to 236ea changed little with H$_2$/HFP ratio. At HFP feed rate of 10 g/h and H$_2$/HFP=5, the conversion of HFP was 97.5%, selectivity to 236ea was 97.6%, and 236ea productivity was about 24 lbs/h/ft$^3$. Also, the catalyst was very stable at high H$_2$/HFP molar ratio. The results are set forth in Table 5.

TABLE 5

(Effect of H$_2$/HFP atomic ratio on the activity, selectivity and productivity of 5% Ni/C catalyst)

| H$_2$/HFP molar ratio | HFP conversion (%) | 236ea selectivity (%) | 236ea productivity (lb/h/ft$^3$) |
|---|---|---|---|
| 1.2 | 79.0 | 98.2 | 19.6 |
| 2 | 83.4 | 95.9 | 20.3 |
| 5 | 97.5 | 97.6 | 24.1 |

*Reaction conditions: 25 ml catalyst; 100° C.; HFP feed rate: 10 g/h; catalyst reduced at 400° C. Reacted for 10 hrs.

In view of the foregoing examples, it is apparent that some metal catalysts, such as Ni/C, are active and selective for the hydrogenation reactions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

What is claimed is:

1. A process for producing hydrofluorocarbons represented by the following formula I:

wherein m is 0 or 2; n is 0 or 2; and m+n=2, comprising: contacting hydrogen with a compound represented by the following formula II:

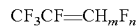

wherein m is 0 or 2; n is 0 or 2; and m+n=2 in the presence of a metal catalyst selected from the group consisting of Fe, Co, Ni, Cu, Cr, Ru, Rh, Ag, Re, Os, Ir, Pt, Au, Sn, and any combination thereof, and wherein m and n of the compound of formula II and hydrofluorocarbon of formula I have a same value.

2. The process of claim 1, wherein m=0 and n=2, and wherein the hydrofluorocarbon is 1,1,1,2,3,3-hexafluoropropane.

3. The process of claim 1, wherein m=2 and n=0, and wherein the hydrofluorocarbon is 1,1,1,2-tetrafluoropropane.

4. The process of claim 1, wherein the catalyst is a supported catalyst.

5. The process of claim 4, wherein the support is selected from the group consisting of: C, Al$_2$O$_3$, SiO$_2$, MgO, ZrO$_2$, TiO$_2$, ZnO, CeO$_2$, La$_2$O$_3$, a metal fluoride, and BaSO$_4$.

6. The process of claim 5, wherein the catalyst is nickel supported on an activated carbon.

7. The process of claim 4, wherein the metal loading on the support is about 0.01 wt % to about 50 wt %.

8. The process of claim 7, wherein the metal loading on the support is about 0.1 wt % to about 25 wt %.

9. The process of claim 8, wherein the metal loading on the support is about 1 wt % to about 10 wt %.

10. The process of claim 1, wherein the catalyst is calcined at about 200° C. to about 500° C. prior to being contacted with hydrogen.

11. The process of claim 1, wherein the catalyst is calcined at about 200° C. to about 600° C. prior to being contacted with hydrogen.

12. The process of claim 1, wherein the catalyst is calcined at about 350° C. to about 500° C. prior to being contacted with hydrogen.

13. The process of claim 1, wherein reaction temperature is about −30° C. to about 500° C.

14. The process of claim 1, wherein reaction pressure is about 0.01 atm to about 100 atm.

15. The process of claim 1, wherein the contact time is from about 0.0001 second to about 100 hours.

16. The process of claim 1, wherein hydrogen to $CF_3CF = CH_mF_n$ molar ratio ranges from about 0.5 to about 20.

17. The process of claim 1, wherein the process is carried out in a reactor selected from the group consisting of: a continuous fixed-bed reactor, a trickle-bed reactor, a moving-bed reactor, a batch reactor, and a CSTR.

18. The process of claim 1, wherein the contacting is carried out in a batch manner.

19. The process of claim 1, wherein the contacting is carried out in a continuous manner.

20. The process of claim 1, wherein the contacting is carried out when the $CF_3CF = CH_mF_n$ compound is in vapor phase.

21. The process of claim 1, wherein the contacting is carried out when the $CF_3CF = CH_mF_n$ compound is in liquid phase.

22. The process of claim 1, wherein the feed is diluted with an inert gas, a target product and/or a recycle stream, and any combination thereof.

23. The process of claim 1, wherein the catalyst is diluted by bare support or metal packings.

24. The process of claim 1, wherein at least a portion of the hydrofluorocarbon and any unreacted hydrogen is recycled.

25. The process of claim 1, wherein the catalyst is an unsupported catalyst.

26. The process of claim 1, wherein the catalyst is Raney Ni or Cu—Cr.

27. A process for producing 1,1,1,2-tetrafluoropropane, comprising contacting hydrogen with 1,1,1,2-tetrafluoropropene in the presence of a Pd catalyst.

28. The process in claim 27, wherein the catalyst is palladium supported on an activated carbon.

* * * * *